(12) United States Patent
Ibarra et al.

(10) Patent No.: US 9,936,982 B2
(45) Date of Patent: Apr. 10, 2018

(54) SYSTEM AND METHOD FOR TRANSLATERAL LINKING OF BILATERAL SPINAL FIXATION RODS

(71) Applicants: Matthew Ibarra, Lakewood, CA (US); Craig Henshaw, Charlestown, MA (US); Jeremy Crossgrove, Storrs, CT (US); Aaron Ricica, Brookline, MA (US); Elizabeth Elidias, Beverly, MA (US); Carin Campbell, Beverly, MA (US)

(72) Inventors: Matthew Ibarra, Lakewood, CA (US); Craig Henshaw, Charlestown, MA (US); Jeremy Crossgrove, Storrs, CT (US); Aaron Ricica, Brookline, MA (US); Elizabeth Elidias, Beverly, MA (US); Carin Campbell, Beverly, MA (US)

(73) Assignee: SPINEFRONTIER, INC, Malden, MA (US)

( * ) Notice: Subject to any disclaimer, the term of this patent is extended or adjusted under 35 U.S.C. 154(b) by 171 days.

(21) Appl. No.: 14/089,293

(22) Filed: Nov. 25, 2013

(65) Prior Publication Data
US 2014/0148856 A1    May 29, 2014

Related U.S. Application Data

(60) Provisional application No. 61/729,663, filed on Nov. 26, 2012.

(51) Int. Cl.
*A61B 17/70* (2006.01)

(52) U.S. Cl.
CPC .............................. *A61B 17/7052* (2013.01)

(58) Field of Classification Search
CPC .............. A61B 17/052; A61B 17/8042; A61B 17/7049
USPC .......... 606/250–253, 257, 260, 270, 276–279
See application file for complete search history.

(56) References Cited

U.S. PATENT DOCUMENTS

| | | | |
|---|---|---|---|
| 5,716,355 A * | 2/1998 | Jackson et al. | ............... 606/252 |
| 5,928,231 A * | 7/1999 | Klein | ................ A61B 17/7049 |
| | | | 606/60 |
| 6,217,578 B1 | 4/2001 | Crozet et al. | |
| 6,234,705 B1 | 5/2001 | Troxell | |
| 6,238,396 B1 | 5/2001 | Lombardo | |
| 6,283,967 B1 | 9/2001 | Troxell et al. | |

(Continued)

FOREIGN PATENT DOCUMENTS

| | | | | |
|---|---|---|---|---|
| SU | 923532 A1 | 5/1982 | | |
| WO | WO2011069963 | * | 6/2011 | ............ A61B 17/70 |
| WO | WO2011124789 A1 | 10/2011 | | |

*Primary Examiner* — Jacqueline Johanas
*Assistant Examiner* — Tessa Matthews
(74) *Attorney, Agent, or Firm* — AKC Patents, LLC

(57) ABSTRACT

A connector assembly for translateral linking of bilateral spinal fixation rods includes first and second components. The first component has an elongated body having first and second ends, and the first end of the first component is configured to connect to a first spinal fixation rod. The second component has an elongated body having first and second ends, and the first end of the second component is configured to connect to a second spinal fixation rod. The second end of the first component is configured to be slidably connected to the second end of the second component.

8 Claims, 15 Drawing Sheets

(56) References Cited

U.S. PATENT DOCUMENTS

| | | |
|---|---|---|
| 6,554,832 B2 | 4/2003 | Shluzas |
| 6,761,721 B2 | 7/2004 | Burgess et al. |
| 6,875,211 B2 | 4/2005 | Nichols et al. |
| 6,887,241 B1 | 5/2005 | McBride et al. |
| 6,958,066 B2 | 10/2005 | Richelsoph et al. |
| 7,104,993 B2 | 9/2006 | Baynham et al. |
| 7,604,652 B2 | 10/2009 | Arnin et al. |
| 7,717,938 B2 | 5/2010 | Kim et al. |
| 7,744,633 B2 | 6/2010 | Berrevoets et al. |
| 7,771,474 B2 | 8/2010 | Cordaro |
| 7,959,653 B2 | 6/2011 | Thramann et al. |
| 8,075,594 B2 | 12/2011 | Purcell |
| 8,221,466 B2 | 7/2012 | Asaad et al. |
| 8,262,701 B2 | 9/2012 | Rathbun et al. |
| 9,408,641 B2 * | 8/2016 | Zhang ............... A61B 17/7023 |
| 2003/0114853 A1 | 6/2003 | Burgess et al. |
| 2005/0228377 A1 | 10/2005 | Chao et al. |
| 2006/0161154 A1 | 7/2006 | McAfee |
| 2006/0241598 A1* | 10/2006 | Khalili ............................ 606/61 |
| 2007/0016197 A1 | 1/2007 | Woods et al. |
| 2007/0173829 A1 | 7/2007 | Drewry et al. |
| 2008/0109039 A1* | 5/2008 | Michielli et al. ............. 606/251 |
| 2009/0105765 A1 | 4/2009 | Strnad |
| 2010/0249842 A1 | 10/2010 | Mir |
| 2010/0274286 A1* | 10/2010 | Blain et al. .................... 606/250 |
| 2010/0298882 A1* | 11/2010 | James ........................... 606/250 |
| 2011/0015679 A1* | 1/2011 | Fiere .................. A61B 17/7001 606/276 |
| 2011/0060367 A1* | 3/2011 | Stauber .............. A61B 17/7049 606/250 |
| 2011/0152934 A1* | 6/2011 | Asaad ........................... 606/250 |
| 2011/0307012 A1 | 12/2011 | Mir et al. |
| 2012/0004688 A1 | 1/2012 | Marino et al. |
| 2012/0035659 A1 | 2/2012 | Barrus et al. |
| 2012/0035728 A1 | 2/2012 | Fallin et al. |
| 2012/0158060 A1 | 6/2012 | Abrahams et al. |
| 2012/0253397 A1* | 10/2012 | Kraus ........................... 606/250 |
| 2014/0128919 A1* | 5/2014 | Okamoto ........... A61B 17/7052 606/252 |

* cited by examiner

US 9,936,982 B2

SYSTEM AND METHOD FOR TRANSLATERAL LINKING OF BILATERAL SPINAL FIXATION RODS

CROSS REFERENCE TO RELATED CO-PENDING APPLICATIONS

This application claims the benefit of U.S. provisional application Ser. No. 61/729,663 filed Nov. 26, 2012 and entitled "SYSTEM AND METHOD FOR TRANSLATERAL LINKING ASSEMBLY OF BILATERAL SPINAL FIXATION RODS", the contents of which are expressly incorporated herein by reference.

FIELD OF THE INVENTION

The present invention relates to a system and a method for a translateral linking assembly, and more particularly to a translateral linking assembly used to support bilateral spinal fixation rods.

BACKGROUND OF THE INVENTION

Several spinal fixation systems exist for stabilizing the spine so that bony fusion is achieved. The majority of these fixation systems use either plates or rods that attach to screws inserted into the vertebral body or the pedicles. Plate fixation systems are more commonly used in the anterior part of the spine, i.e., vertebral bodies, while rods are the accepted standard for posterior fixation. These spine fixation systems can be extended along the sides of the spine by connecting two adjacent pedicles at a time similar to the concept of a bicycle chain.

Single or multilevel segmental posterior fusions are most commonly achieved by contouring a solid ¼-inch cylindrical rod and attaching it to adjacent pedicle screws on each side of the spine using various connecting assemblies. This longitudinal construction can be made more rigid by connecting the rods to each other with a cross-connector (or translateral linking assembly) to form an "H" configuration.

The rod system requires contouring of each rod across several vertebras in many cases. The contouring of each rod depends on the configuration of the pedicle screws and varies from side to side in the same patient and among patients. This may add considerable time to an operation. Recent generations of pedicle screws and rod cross-connectors seek to diminish this drawback by allowing variable axes of movements in the pedicle screw recess for the rod or in the rod connectors. However, in most cases this adds another level of complexity to the operation and often further increases the operative time. This increase in operative time and the complexity of the cross-connectors put substantial stress on the surgeon and the supporting staff. Accordingly, cross-connectors that reduce the complexity level of the spinal stabilization assemblies are desirable.

SUMMARY OF THE INVENTION

The present invention relates to a translateral linking assembly, and more particularly to a translateral linking assembly used to support bilateral spinal fixation rods.

In general, in one aspect, the invention features, a connector assembly for translateral linking of bilateral spinal fixation rods including first and second components. The first component has an elongated body having first and second ends, and the first end of the first component is configured to connect to a first spinal fixation rod. The second component has an elongated body having first and second ends, and the first end of the second component is configured to connect to a second spinal fixation rod. The second end of the first component is configured to be slidably connected to the second end of the second component.

Implementations of this aspect of the invention may include one or more of the following features. The elongated body of the second component further includes a side opening formed at the second end of the second component, and the second end of the first component is configured to be inserted into the side opening of the second end of the second component and is secured to the second end of the second component via a locking setscrew. The length of the connector assembly is adjusted by sliding the first component into or out of the side opening. The elongated body of the first component is flat and plate-shaped and the first end of the first component includes a hook, a clip and a first through-opening, and the first spinal fixation rod is configured to be held in the space between the hook and the clip and to be secured to the first end of the first component via a screw configured to be threaded into the first through-opening of the first end of the first component and to press the clip down onto the first spinal fixation rod. The elongated body of the second component is flat and plate-shaped and the second end of the second component further includes an upward extending dorsal protrusion and the first end of the second component includes a hook, a clip and a first through-opening. The second spinal fixation rod is configured to be held in the space between the hook and the clip and to be secured to the first end of the second component via a screw configured to be threaded into the first through-opening of the first end of the second component and to press the clip down onto the second spinal fixation rod. The dorsal protrusion is flat and has a central through-opening. The connector assembly may further include a dorsal component and the dorsal component comprises a first through-opening formed at the base of the dorsal component and the second ends of the first and second components are configured to be inserted into the first through-opening of the dorsal component and are secured to the dorsal component via a locking setscrew. The length of the connector assembly is adjusted by sliding the first and/or second components into or out of the first through-opening of the dorsal component. The dorsal component extends upward, is flat and comprises a central through-opening and the inner perimeter of the central through opening comprises teeth. The second end of the first component is configured to slide within the first through-opening of the dorsal component on top of the second end of the second component. The second end of the first component is configured to slide within the first through-opening of the dorsal component adjacent to the second end of the second component. The connector assembly may further include a cylindrical component and the cylindrical component comprises a side through-opening and the second ends of the first and second components are configured to be inserted into the side through-opening of the cylindrical component and are secured to the cylindrical component via a locking setscrew. The length of the connector assembly is adjusted by sliding the first and/or second components into or out of the side through-opening of the cylindrical component. The second end of the first component is configured to slide within the side through-opening of the cylindrical component on top of the second end of the second component. The second end of the first component is configured to slide within the side through-opening of the cylindrical component adjacent to the second end of the second component. The cylindrical component further comprises a top through-opening dimensioned to receive the locking setscrew. The first end of the first component further comprises an opening and a protrusion extending upward from the clip and the protrusion is configured to be inserted and lock into the opening when the clip is pressed down onto the first spinal fixation rod. The first end of the second component further comprises an opening and a protrusion extending upward from the clip and the protrusion is configured to be inserted and lock into the opening when the clip is pressed down onto the second spinal fixation rod. The elongated body of the first component is flat, narrow and plate-shaped and the first end of the first component comprises a hook and a first through-opening, and the first spinal fixation rod is configured to be held within the hook and to be secured to the first end of the first component via a set screw configured to be threaded into the first through-opening of the first end of the first component. The elongated body of the second component is flat, narrow and plate-shaped and the first end of the second component comprises a hook and a first through-opening, and the second spinal fixation rod is configured to be held within the hook and to be secured to the first end of the second component via a set screw configured to be threaded into the first through-opening of the first end of the second component. The elongated body of the first component is flat, narrow and plate-shaped and the first end of the first component comprises a side opening and a through-opening and the connector assembly further comprises a first hooked connector and the first hooked connector comprises a hook end, a flat end and a through-opening, and the flat end of the first hooked connector is configured to be inserted into the side opening of the first end of the first component and the through-opening of the hooked connector is arranged concentrically with the through-opening of the first end of the first component. The first spinal fixation rod is configured to be held and secured within the hook end of the first hooked connector and the hooked connector is secured to the first end of the first component via a set-screw configured to be threaded into the concentrically arranged through-openings of the first end of the first component and the hooked connector. The through-opening of the hooked connector is tapered and tightening of the set-screw moves the hooked connector and the first spinal fixation rod towards a midline of the connector assembly. The second end of the second component comprises a cylindrical component and the cylindrical component comprises a side through-opening and the second end of the first component is configured to be inserted into the side through-opening of the cylindrical component and is secured to the cylindrical component via a locking setscrew, and wherein the length of the connector assembly is adjusted by sliding the first component into or out of the side through-opening of the cylindrical component.

In general, in another aspect, the invention features, a method for translateral linking of bilateral spinal fixation rods including the following. First, providing a first component comprising an elongated body having first and second ends, and connecting the first end of the first component to a first spinal fixation rod. Next, providing a second component comprising an elongated body having first and second ends, and connecting the first end of the second component to a second spinal fixation rod. Next, connecting slidably the second end of the first component to the second end of the second component.

The details of one or more embodiments of the invention are set forth in the accompanying drawings and description below. Other features, objects, and advantages of the invention will be apparent from the following description of the preferred embodiments, the drawings, and the claims

BRIEF DESCRIPTION OF THE DRAWINGS

Referring to the figures, wherein like numerals represent like parts throughout the several views.

DETAILED DESCRIPTION OF THE INVENTION

The present invention relates to a translateral linking assembly, and more particularly to a translateral linking assembly used to support bilateral spinal fixation rods.

Figure 1A:
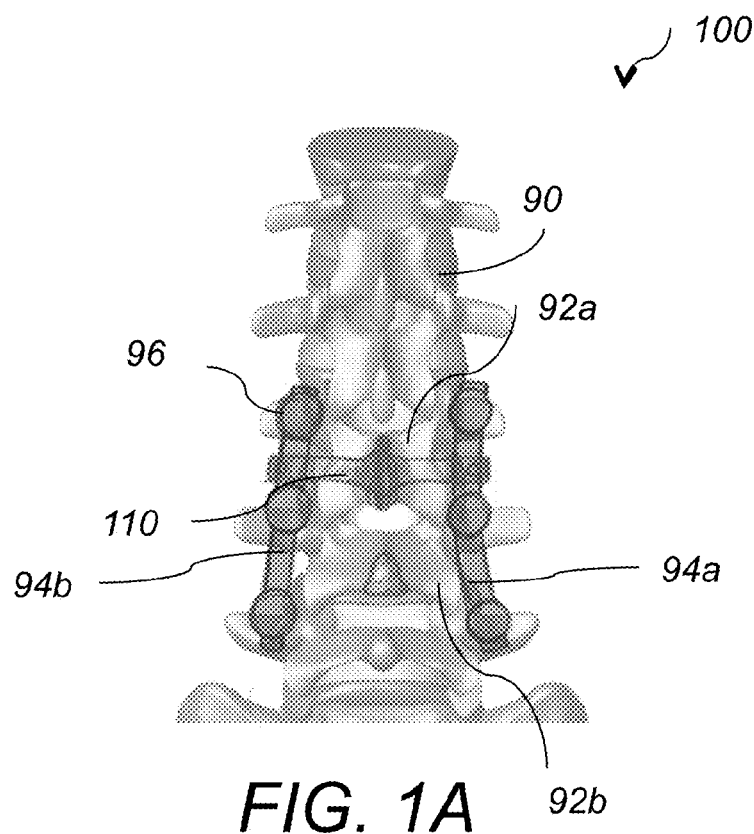
FIG. 1A is a front schematic view of a spinal fixation assembly, according to this invention.
Figure 1B:
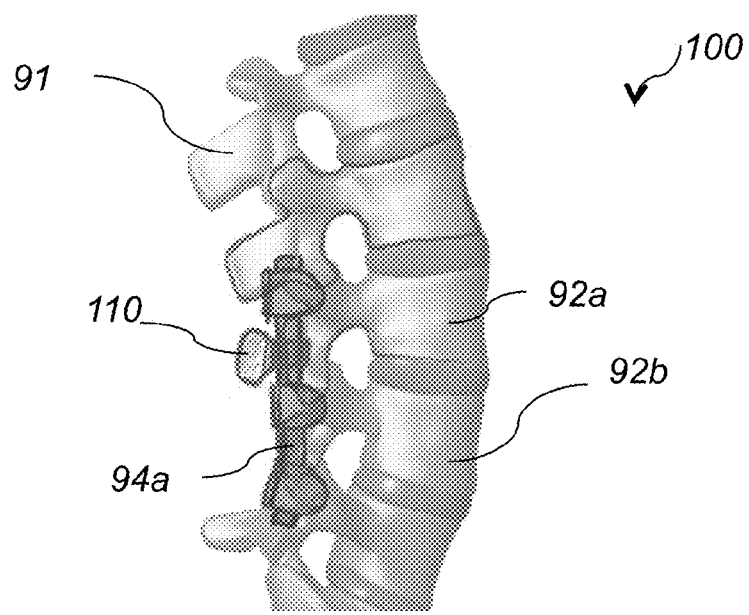
FIG. 1B is a side schematic view of the spinal fixation assembly of FIG. 1A.

Referring to FIG. 1A, spinal fixation assembly 100 includes two bilateral spinal fixation rods 94a, 94b and a translateral linking assembly 110. Rods 94a, 94b are attached to the right and left sides of two adjacent spinal vertebras 92a, 92b with screws 96. Translateral linking assembly 110 extends perpendicular to rods 92a, 92b and connects them.

Figure 2A:
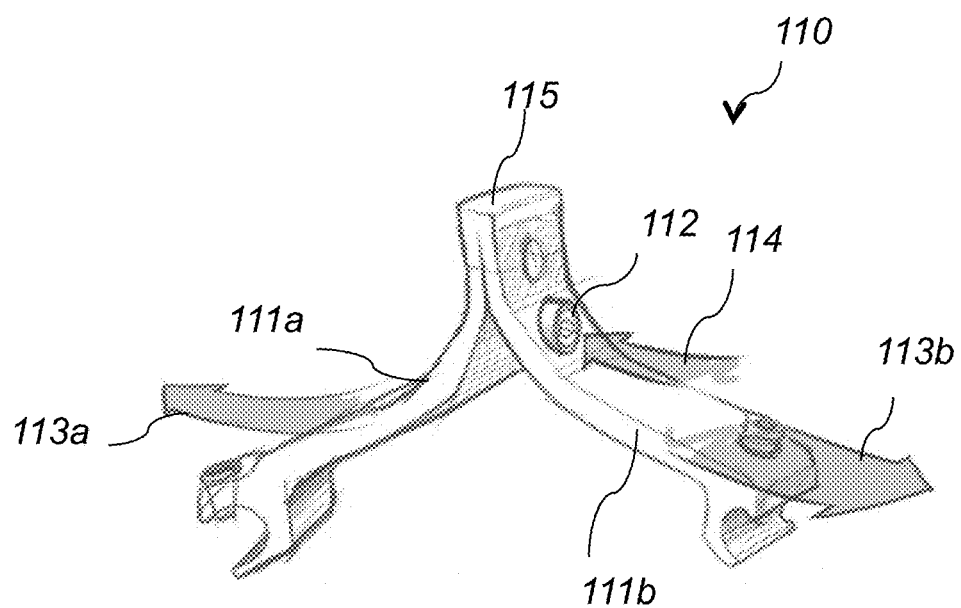
FIG. 2A is a schematic perspective view of the translateral linking assembly of FIG. 1A in the "engaged or stretched position"
Figure 2B:
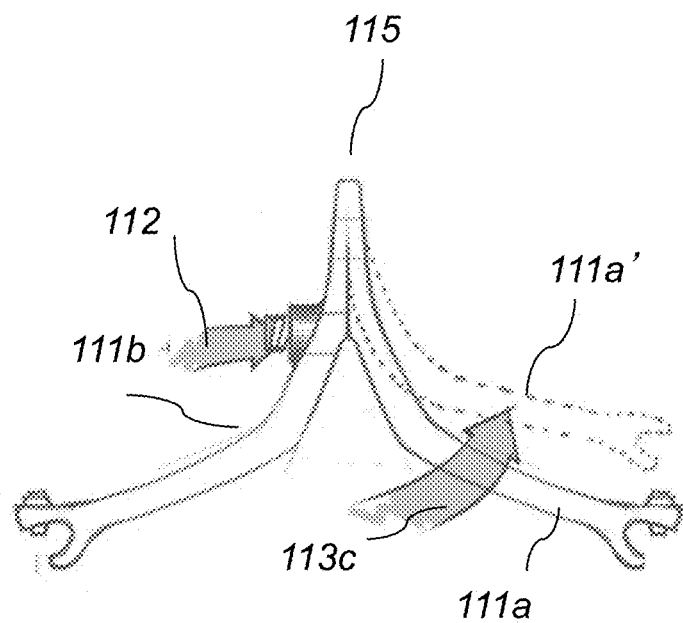
FIG. 2B is a schematic perspective view of the translateral linking assembly of FIG. 1A in the "non-engaged or non-stretched position"
Figure 3A:
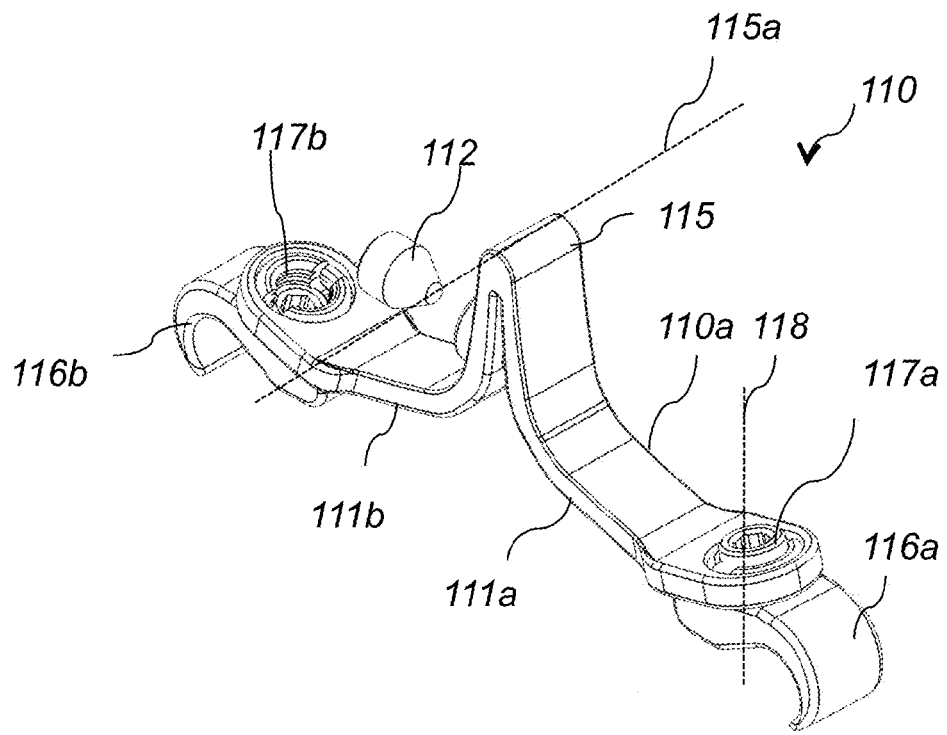
FIG. 3A is a perspective view of the translateral linking assembly of FIG. 1A.
Figure 3B:
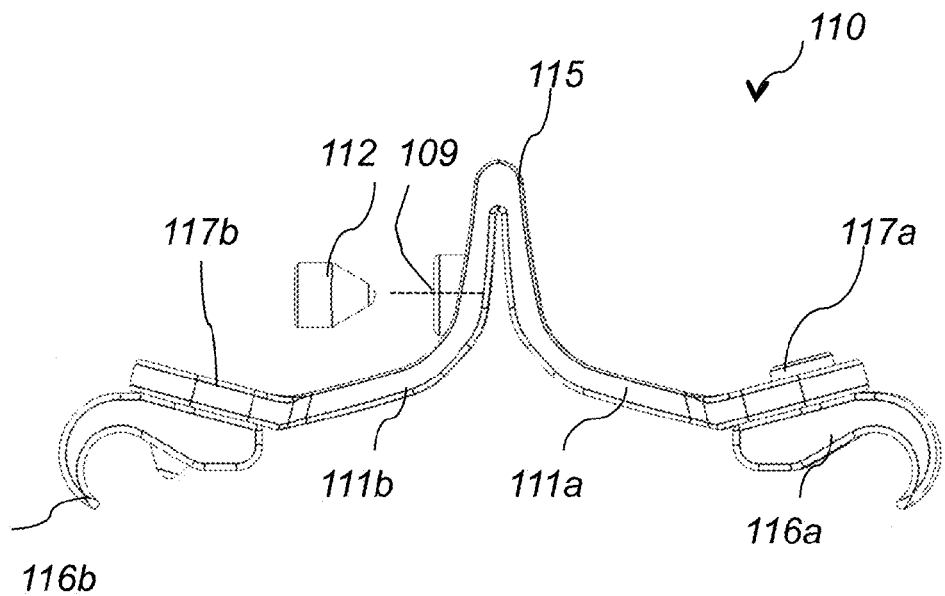
FIG. 3B is a front view of the translateral linking assembly of FIG. 1A.

Referring to FIG. 2A, and FIG. 3A linking assembly 110 includes an A-shaped main body 110a and left and right rod connectors 116b, 116a. The A-shaped main body 110a has a slightly arched protrusion 115 along the midline 115a and left and right extending components 111b, 111a that are jointed along the midline 115a. Main body 110a also includes a screw 112 configured to be threaded through an opening 109 in one of the two components 111b, as shown in FIG. 3B. When screw 112 is threaded into opening 109, it compresses the two components 111b, 111a along direction 114 near the midline 115a and extends the two components 111b, 111a laterally along directions 113b, 113a, respectively. The opposite motion occurs when screw 112 is disengaged from opening 109. In this case, components 111b, 111a move in the non-extended position. FIG. 2B depicts the extended position of components 111a and 111b and the non-extended position (111a') of component 111a.

Figure 3C:
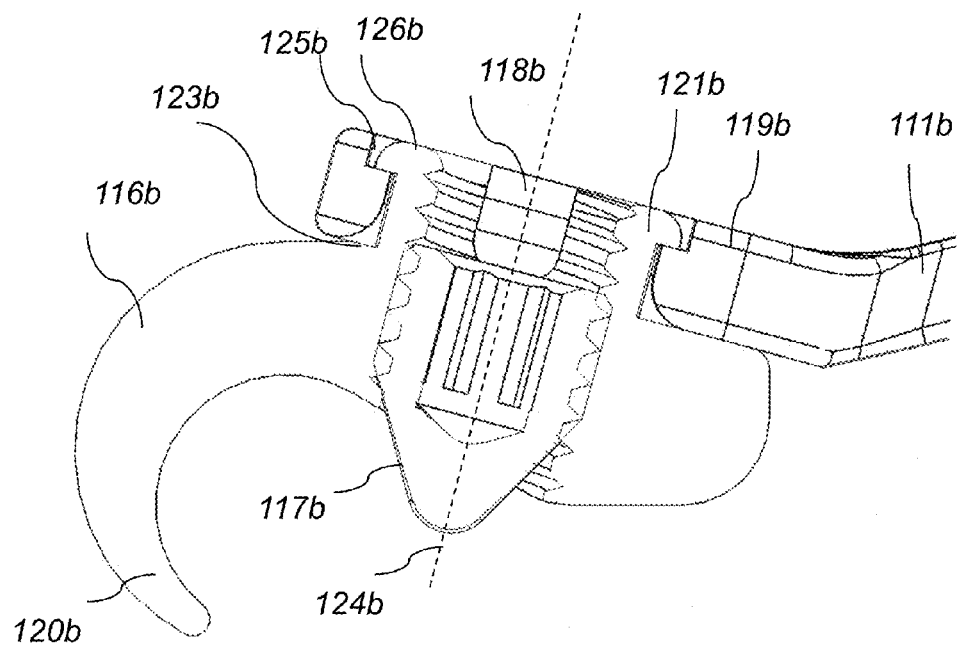
FIG. 3C is a partial cross-sectional view of the rod connector in the translateral linking assembly of FIG. 1A.

Rod connectors 116b, 116a are hook-shaped and are pivotally connected to the free ends 119b, 119a of components 111b, 111a, respectively. Referring to FIG. 3C, each rod connector 116b, 116a includes an upward oriented protrusion 121b and a hook end 120b. Protrusion 121b has a through-opening 118b configured to receive a set screw 117b, as shown in FIG. 3C. Free end 119b of component 111b has a through-opening 123b, shaped and dimensioned to receive and pivotally engage protrusion 121b of the rod connector 116b. In one example, opening 123b has a cutout 125b that is shaped and dimensioned to receive a lateral protrusion 126b of protrusion 121b and thereby to pivotally connect end 119b to rod connector 116b. This pivoting engagement allows the rod connector 116b and the attached rod 94b to be positioned at any angular orientation around axis 124b relative to the linking assembly 110. Once the desired orientation is selected, set screw 117b is threaded through opening 118b. Set screw 117b distracts the perimeter of through opening 118b and presses down onto the rod 94b and thereby secures the orientation of the rod connector 116b relative to the free end 119b and locks rod 94b onto the rod connector 116b, respectively. The same symmetric arrangement is also valid between rod connector 116a, free end 119a of component 111a and rod 94a.

Figure 4E:
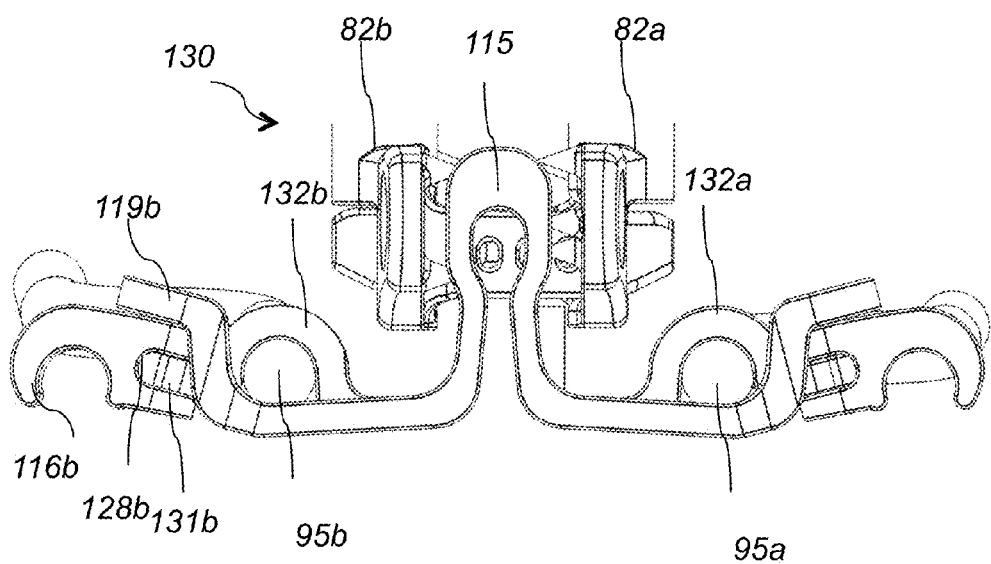
FIG. 4E is a front view of the translateral linking assembly of FIG. 4B.
Figure 4A:
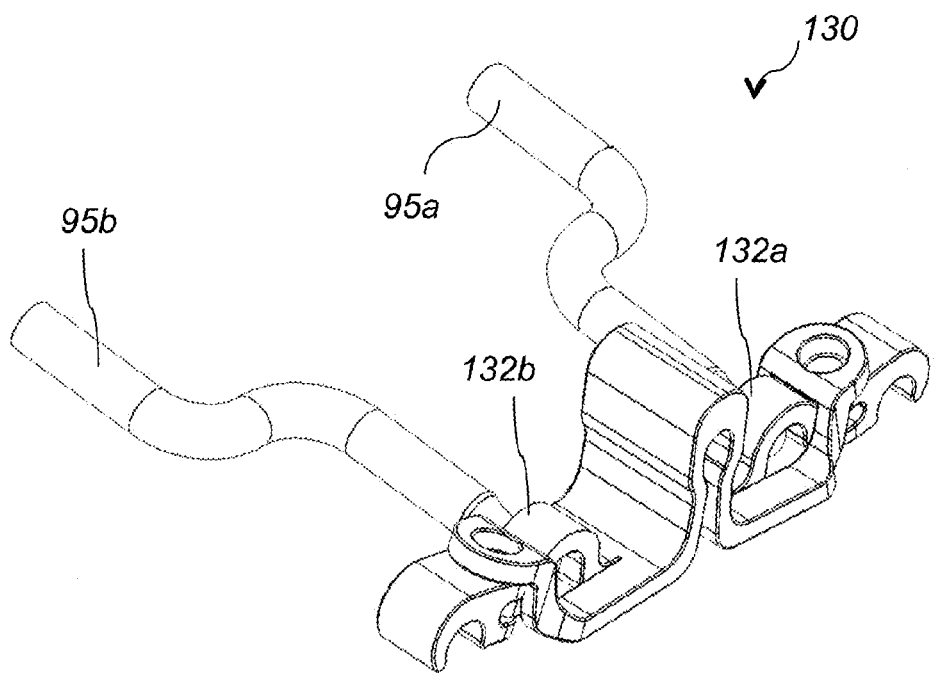
FIG. 4A and FIG. B are right side perspective views of another embodiment of the translateral linking assembly, according to this invention.
Figure 4B:
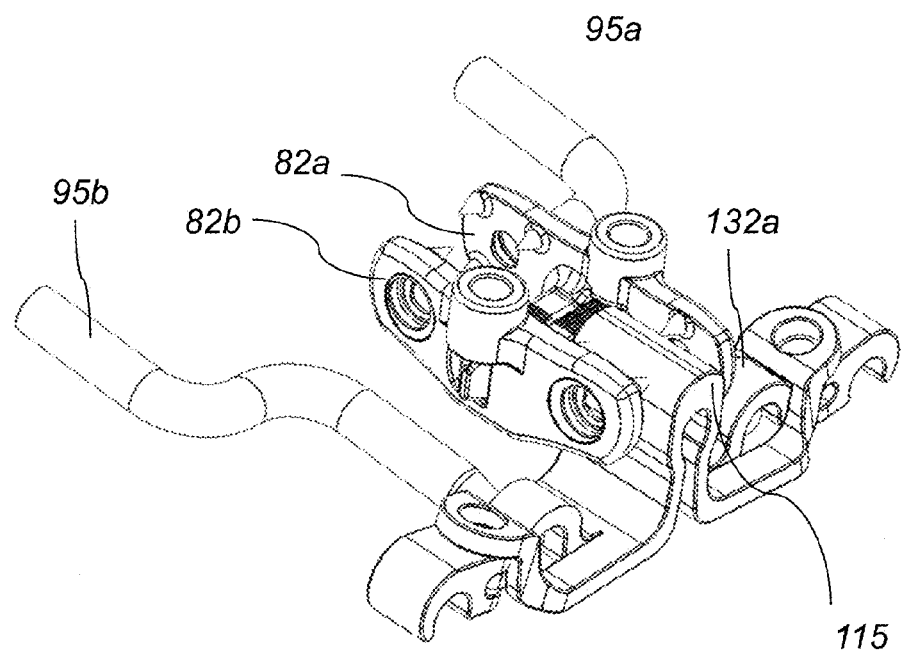
FIG. 4C is a front view of the translateral linking assembly of FIG. 4A.
FIG. 4D is a perspective view of the translateral linking assembly of FIG. 4A.
Figure 4C:
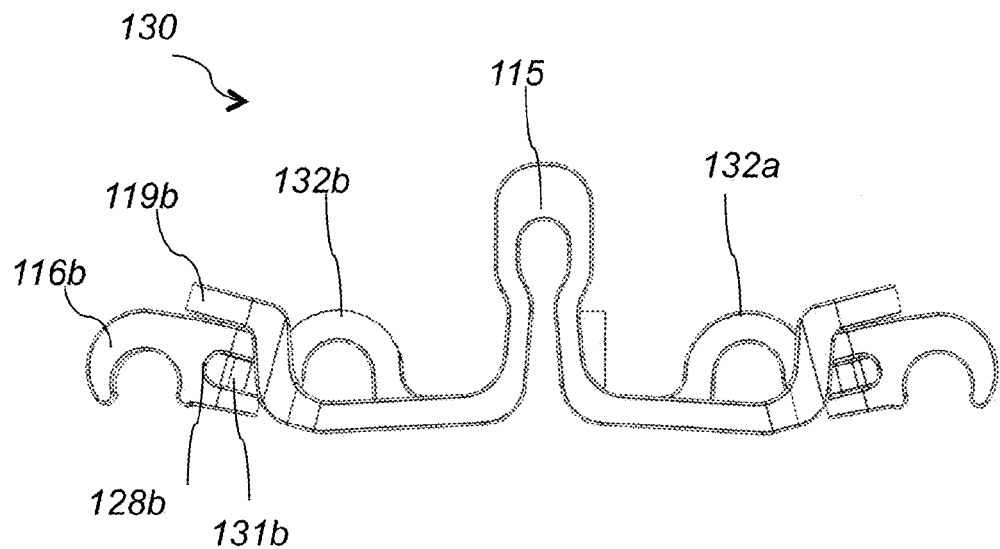
Figure 4D:
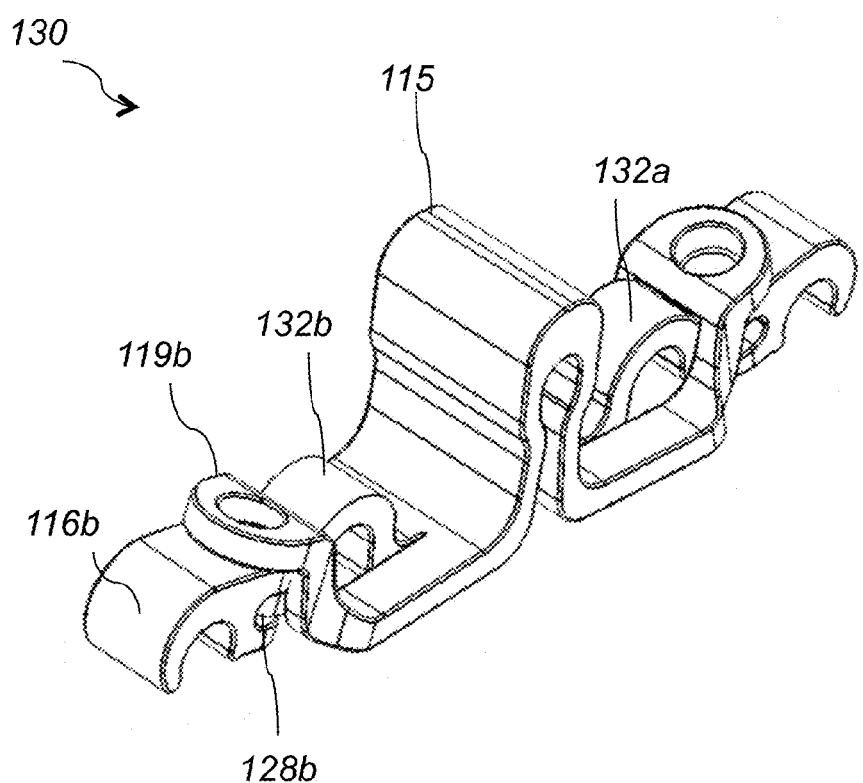

Referring to FIG. 4A, in another embodiment, translateral linking assembly 130 supports four rods 94a, 94b, 95a, 95b. Translateral linking assembly 130 further includes loop elements 132a, 132b that are attached to components 111a, 111b, respectively. Loop elements 132a, 132b are dimensioned to receive rods 95a, 95b, respectively. A spinous process fixation device 82a, 82b is also attached to the side surfaces of arched protrusion 115, as shown in FIG. 4B. In this embodiment, rod connector 116b further includes a side opening 128b dimensioned to receive a side extension 131b of loop element 132b, as shown in FIG. 4C, FIG. 4D and FIG. 4E. A symmetric second side extension of loop 132b is inserted into an opening formed within component 111b (not shown). The attachment of rod 94b to the rod connector 116b is the same as in the embodiment of FIG. 3C. However, in this case, set screw 117b also presses extension 131b down and thereby secures the end of rod 95b within loop element 132b and onto component 111b. The same symmetric arrangement is also valid between rod 95a, loop element 132a component 111a and set screw 117a. Rods 95a, 95b have ball-shaped tips that allows them to have poly-axial orientations.

Figure 5A:
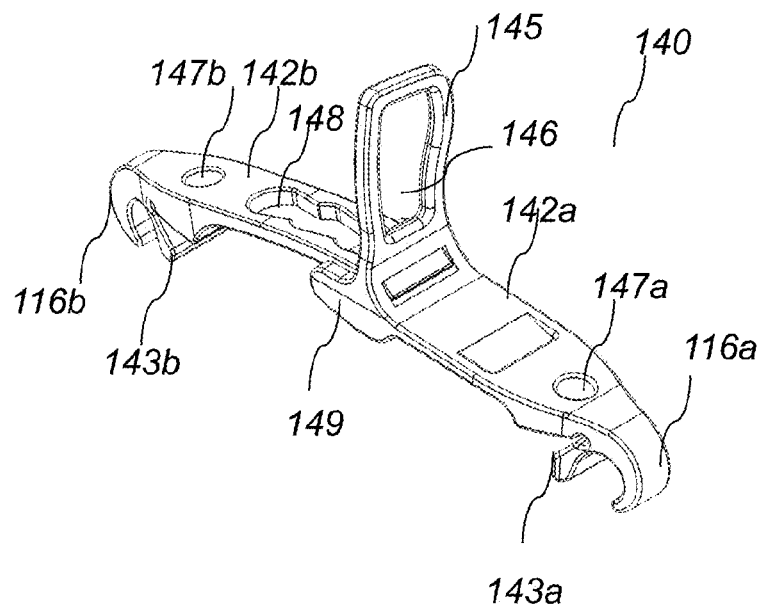
FIG. 5A is a perspective view of another embodiment of the translateral linking assembly, according to this invention.
Figure 5B:
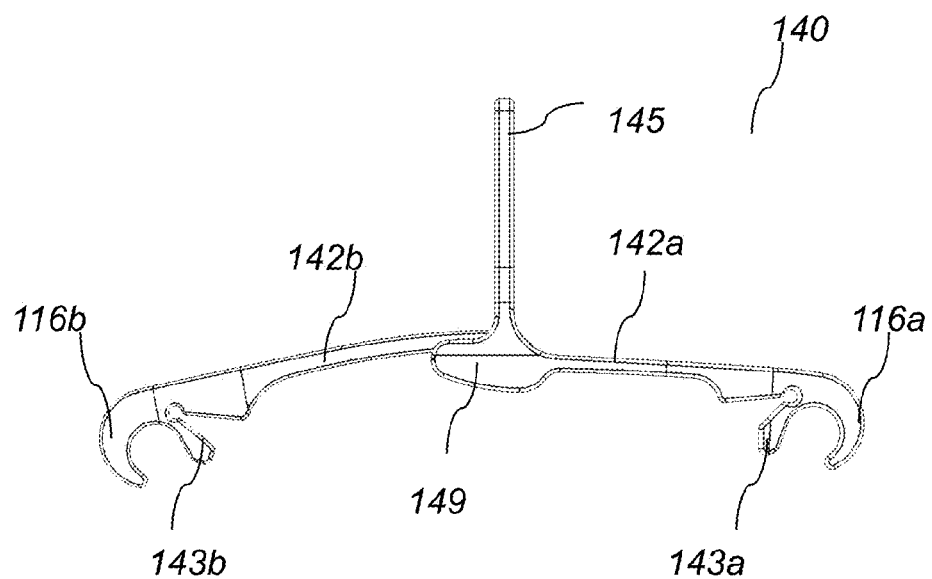
FIG. 5B is a front view of the translateral linking assembly of FIG. 5A.
Figure 5C:
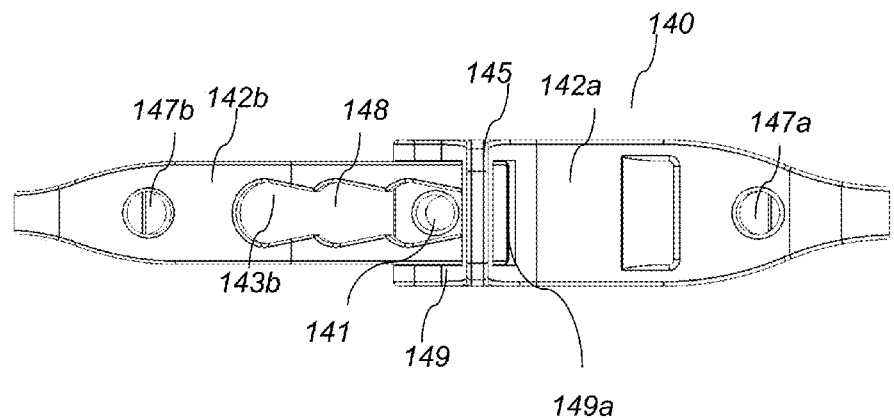
FIG. 5C is a top view of the translateral linking assembly of FIG. 5A.
Figure 8E:
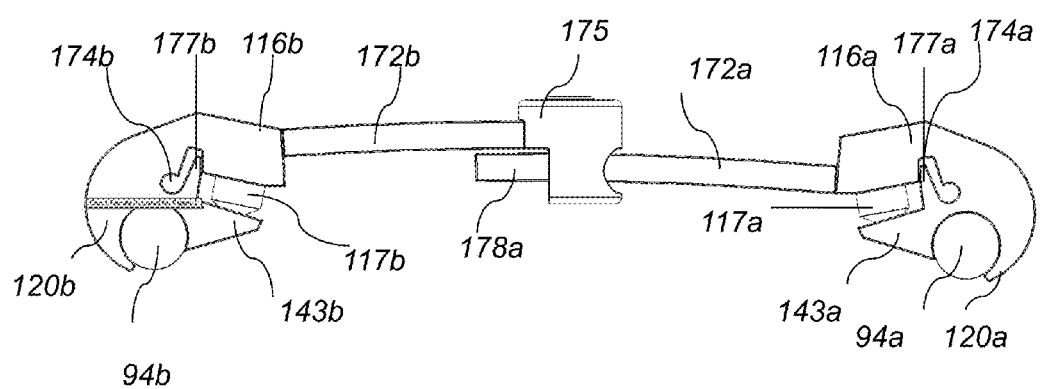
FIG. 8E is a side view of the translateral linking assembly of FIG. 8A in the rod engaged position.
Figure 8A:
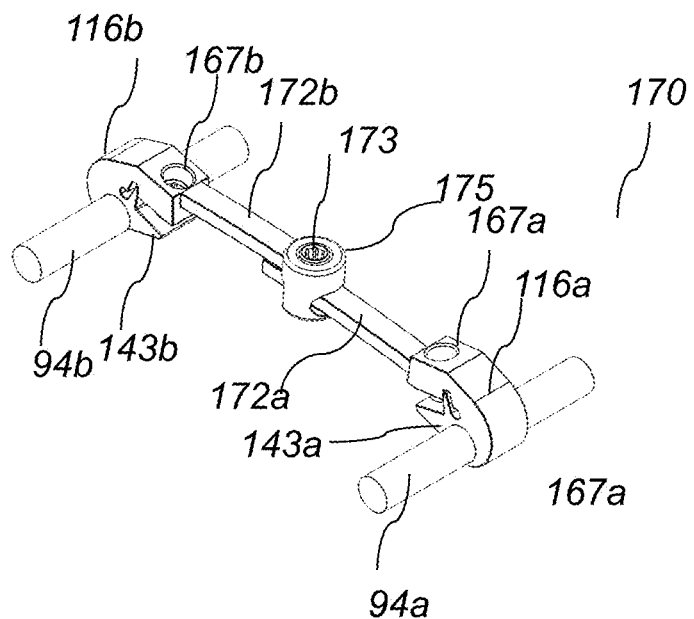
FIG. 8A is a perspective view of another embodiment of the translateral linking assembly, according to this invention.
Figure 8B:
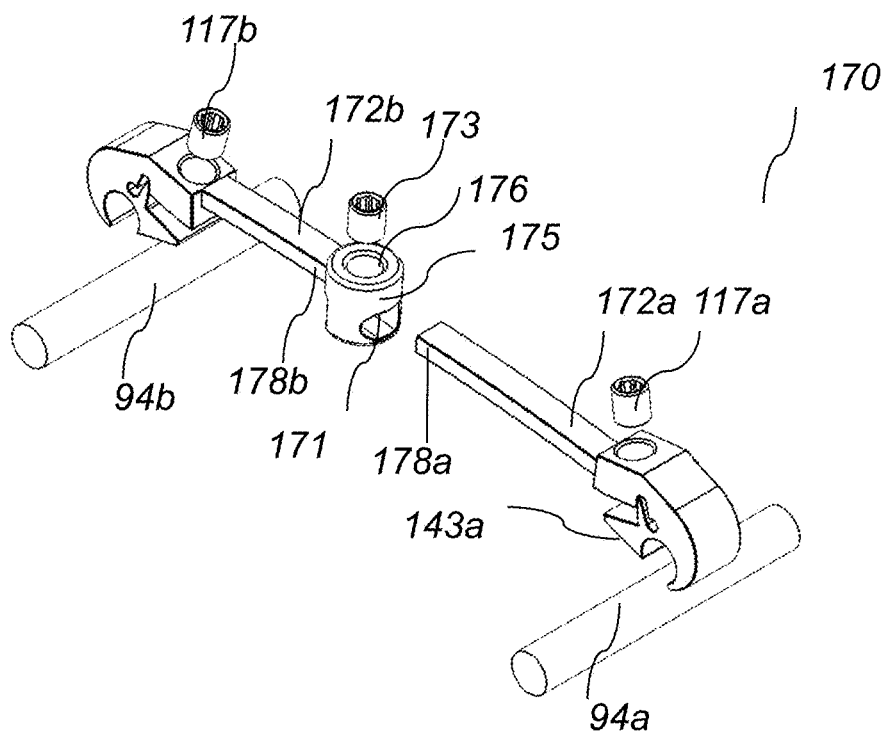
FIG. 8B is a perspective view of the translateral linking assembly of FIG. 8A in the rod non-engaged position.
Figure 8C:
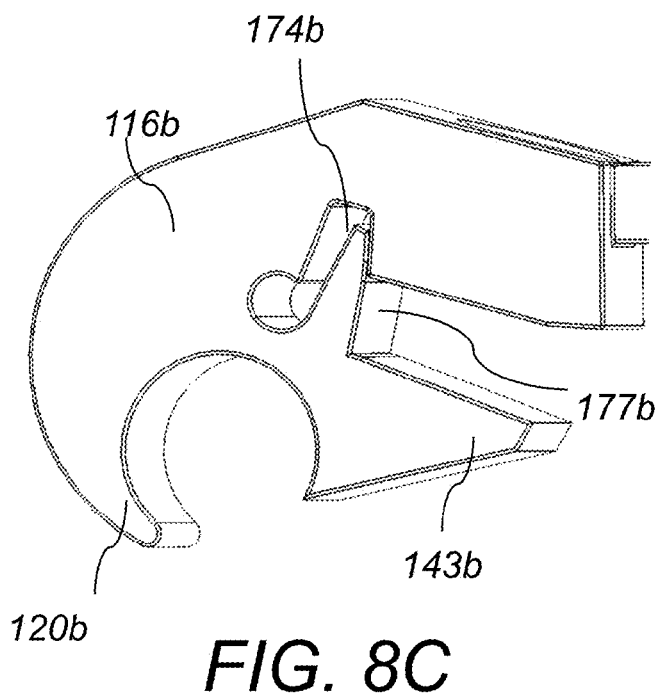
FIG. 8C is an enlarged view of the hook connector in the assembly of FIG. 8A in the rod non-engaged position.
Figure 8D:
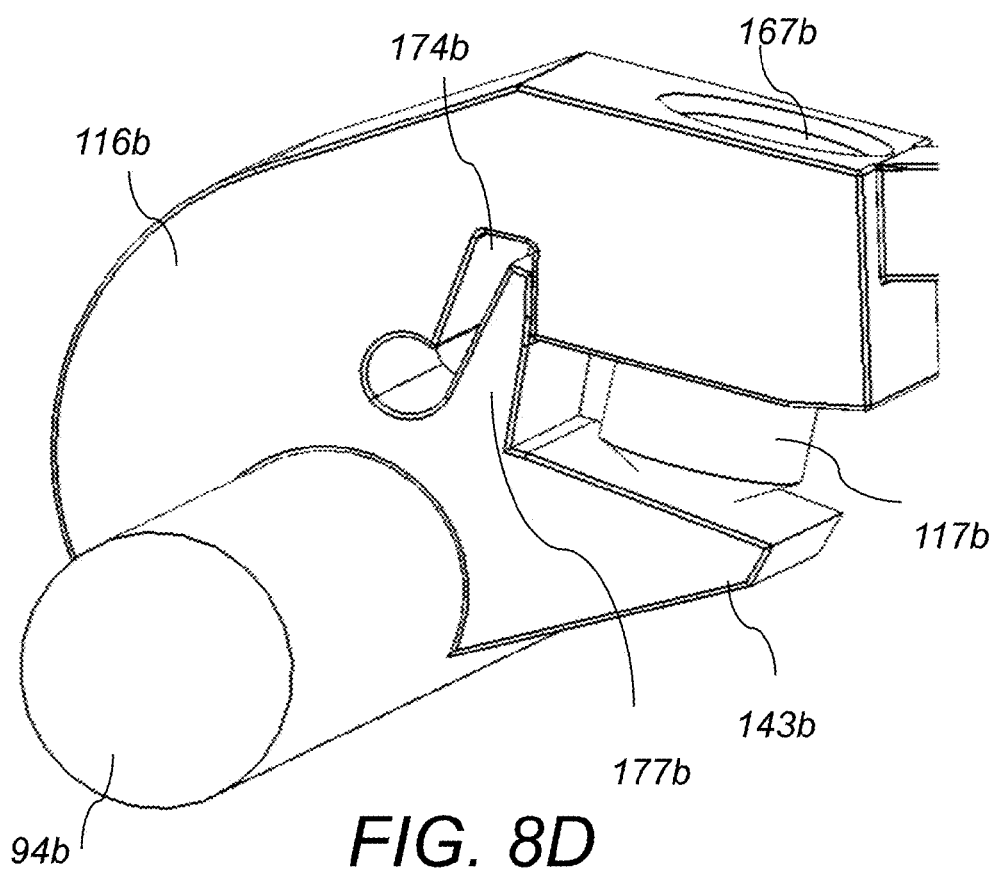
FIG. 8D is an enlarged view of the hook connector in the assembly of FIG. 8A in the rod engaged position.

Referring to FIG. 5A, FIG. 5B and FIG. 5C, in another embodiment, translateral linking assembly 140 includes a main body that is made of two separate components 142a, 142b that are slidably connected to each other at the midpoint. In this case, component 142b is inserted into a side opening 149a formed in the end 149 of component 142a and is secured with a locking setscrew 141. The length of the linking assembly 140 is adjusted by sliding component 142b into or out of the opening 149a in component 142a. End 149 of component 142a also includes an upward extending dorsal protrusion 145 that is flat, and has a central through-opening 146. Components 142a, 142b are flat, plate like and terminate into hooked rod connectors 116a, 116b, respectively. Hooked rod connectors 116a, 116b include hook ends 120a, 120b and clips 143a, 143b, respectively. Rods 94a, 94b are held in the space defined by the hooks 116a, 116b and clips 143a, 143b, respectively, and are secured by set screws 117a, 117b (shown in FIG. 8B) that are screwed into openings 147a, 147b and press clips 143a, 143b down and around the rods 94a, 94b, respectively.

Figure 6C:
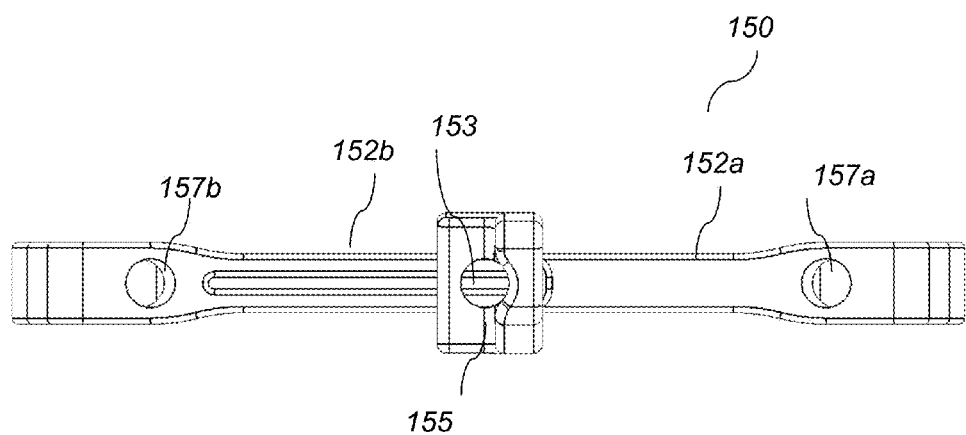
FIG. 6C is a top view of the translateral linking assembly of FIG. 6A.
Figure 6A:
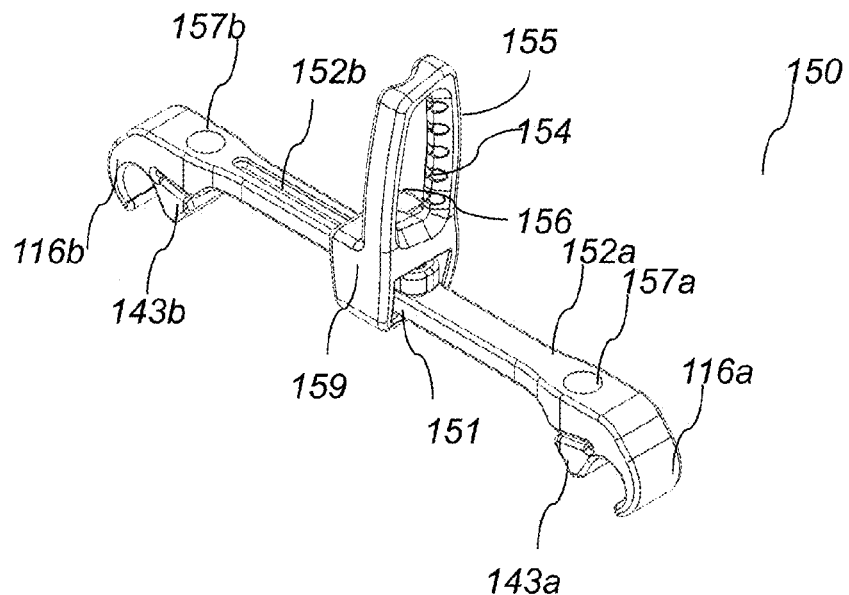
FIG. 6A is a perspective view of another embodiment of the translateral linking assembly, according to this invention.
Figure 6B:
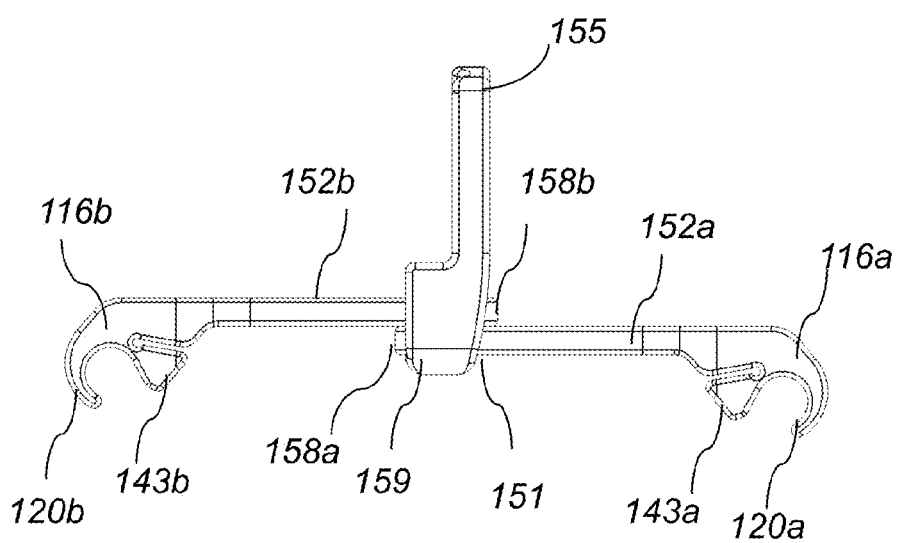
FIG. 6B is a front view of the translateral linking assembly of FIG. 6A.

Referring to FIG. 6A, FIG. 6B and FIG. 6C, in another embodiment, translateral linking assembly 150 includes a main body that is made of two separate components 152a, 152b that are slidably connected to a dorsal component 155. In this case, the ends 158a, 158b of components 152a and 152b are inserted into an opening 151 formed in the bottom 159 of dorsal component 155 and are secured with a locking setscrew 153. End 158b slides on top of end 158a and both ends 158a, 158b slide into and out of opening 151. The length of the linking assembly 150 is adjusted by sliding components 152a, 152b into or out of the opening 151. Dorsal component 155 extends upward, is flat, and has a central through-opening 156. The inner perimeter of opening 156 includes teeth 154. Components 152a, 152b are flat, narrow, plate like and terminate into hooked rod connectors 116a, 116b, respectively. Hooked rod connectors 116a, 116b include hook ends 120a, 120b and clips 143a, 143b, respectively. Rods 94a, 94b are held in the space defined by the hooks 116a, 116b and clips 143a, 143b, respectively, and are secured by set screws 117a, 117b that are screwed into openings 157a, 157b and press clips 143a, 143b down and around the rods 94a, 94b, respectively. In this embodiment, the dorsal component 155 is first placed along the midline of the spine and then the two lateral components 152a, 152b are inserted into opening 151.

Figure 7A:
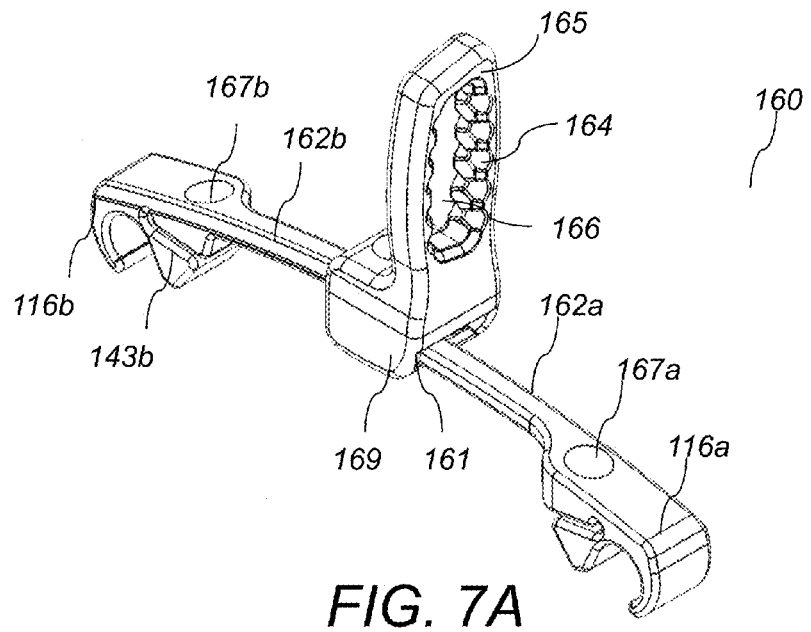
FIG. 7A is a perspective view of another embodiment of the translateral linking assembly, according to this invention.
Figure 7B:
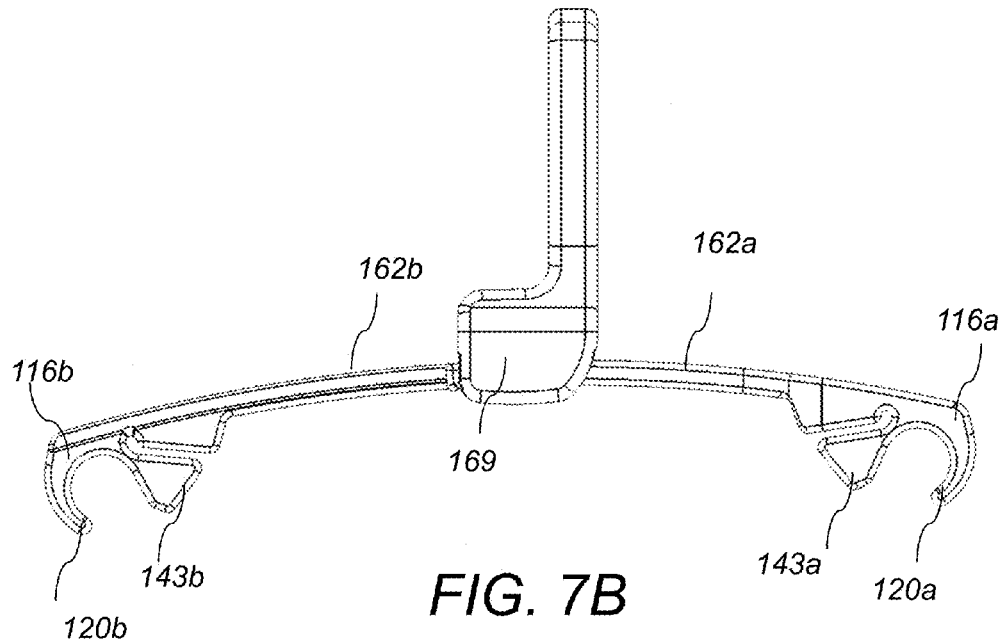
FIG. 7B is a front view of the translateral linking assembly of FIG. 7A.
Figure 7C:
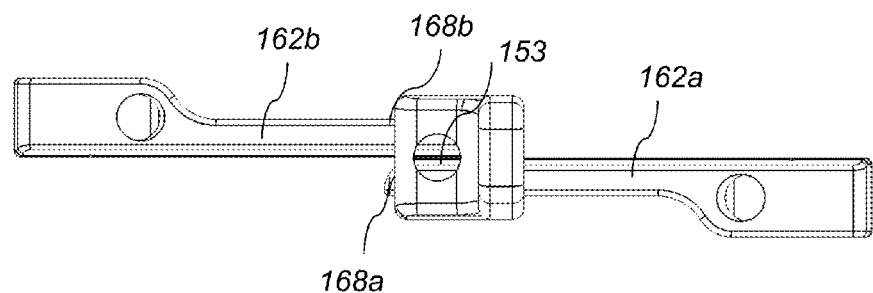
FIG. 7C is a top view of the translateral linking assembly of FIG. 6A.

Referring to FIG. 7A, FIG. 7B and FIG. 7C, in another embodiment, translateral linking assembly 160 includes a main body that is made of two separate components 162a, 162b that are slidably connected to a dorsal component 165. In this case, the ends 168a, 168b of components 162a and 162b are inserted into an opening 161 formed in the bottom 169 of dorsal component 165 and are secured with a locking setscrew 153. End 168b slides next to end 168a and both ends 168a, 168b slide into and out of opening 161. The length of the linking assembly 160 is adjusted by sliding components 162a, 162b into or out of the opening 161. Dorsal component 165 extends upward, is flat, and has a central through-opening 166. The inner perimeter of opening 166 includes teeth 164. Dorsal component 165 is used as a prosthetic for replacing the spinous process, or as a connector device for an adjacent interspinous plate or for suturing tissue onto it, among others. Components 162a, 162b are flat, narrow, plate like and terminate into hooked rod connectors 116a, 116b, respectively. Hooked rod connectors 116a, 116b include hook ends 120a, 120b and clips 143a, 143b, respectively. Rods 94a, 94b are held in the space defined by the hooks 116a, 116b and clips 143a, 143b, respectively, and are secured by set screws 117a, 117b that are screwed into openings 167a, 167b and press clips 143a, 143b down and around the rods 94a, 94b, respectively. In this embodiment, the dorsal component 165 is first placed along the midline of the spine and then the two lateral components 162a, 162b are inserted into opening 161.

Referring to FIG. 8A, FIG. 8B, FIG. 8C, FIG. 8D, and FIG. 8E, in another embodiment, translateral linking assembly 170 includes a main body that is made of two separate components 172a, 172b that are slidably connected to a cylindrical component 175. In this case, the ends 178a, 178b of components 172a and 172b are inserted into a side opening 171 formed in the cylindrical component 175 and are secured with a locking setscrew 173. End 178b slides on top of end 178a and both ends 178a, 178b slide into and out of opening 171. The length of the linking assembly 170 is adjusted by sliding components 172a, 172b into or out of the opening 171. Cylindrical component 175 also has a top through-opening 176, dimensioned to receive setscrew 173. Components 172a, 172b are flat, narrow, plate like and terminate into hooked rod connectors 116a, 116b, respectively. Hooked rod connectors 116a, 116b include hook ends 120a, 120b and clips 143a, 143b, respectively. Rods 94a, 94b are held in the space defined by the hooks 116a, 116b and clips 143a, 143b, respectively, and are secured by set screws 117a, 117b that are screwed into openings 167a, 167b and press clips 143a, 143b down and around the rods 94a, 94b, respectively. In this embodiment, clips 143a, 143b also include protrusions 177a, 177b that are inserted and pressed into openings 174a, 174b formed in the bottom surfaces of rod connectors 116a, 116b, respectively. In other embodiments, cylindrical component 175 forms the end 178b of component 172b. In these embodiments, the end 178a of component 172a is inserted into side opening 171 of the cylindrical component 175 and is secured with the setscrew 173.

Figure 9A:
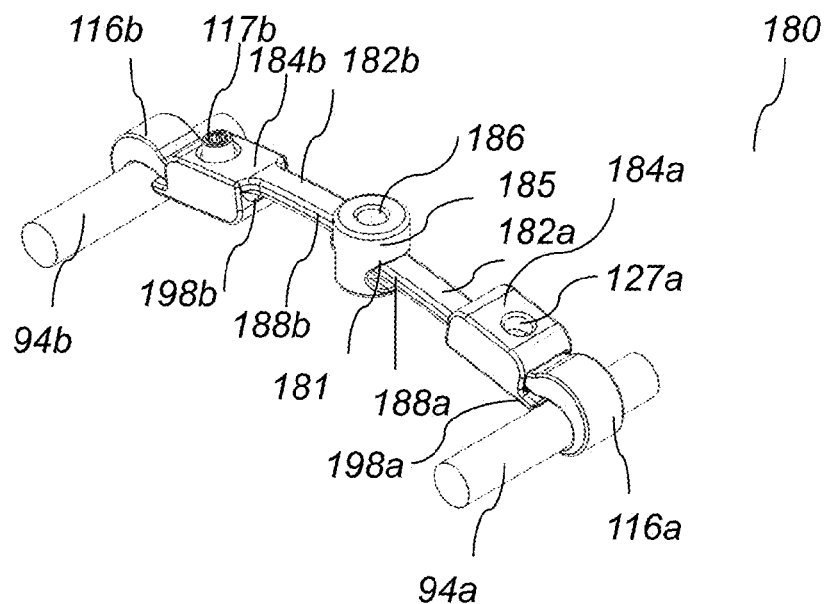
FIG. 9A is a perspective view of another embodiment of the translateral linking assembly, according to this invention.
Figure 9B:
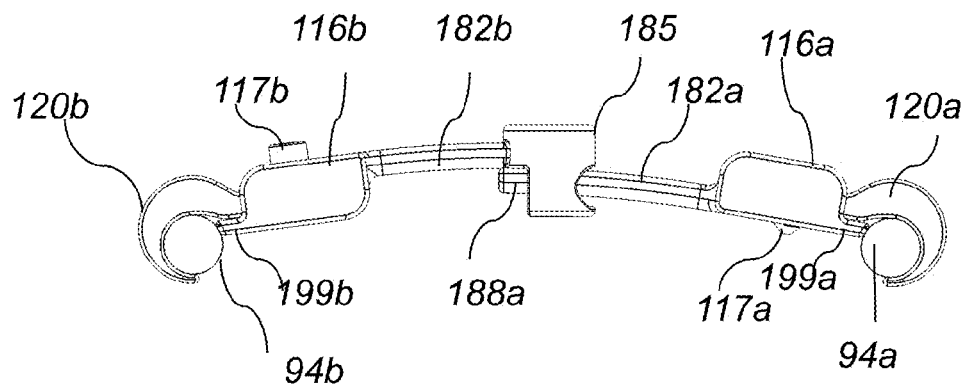
FIG. 9B is a front view of the translateral linking assembly of FIG. 9A.
Figure 9C:
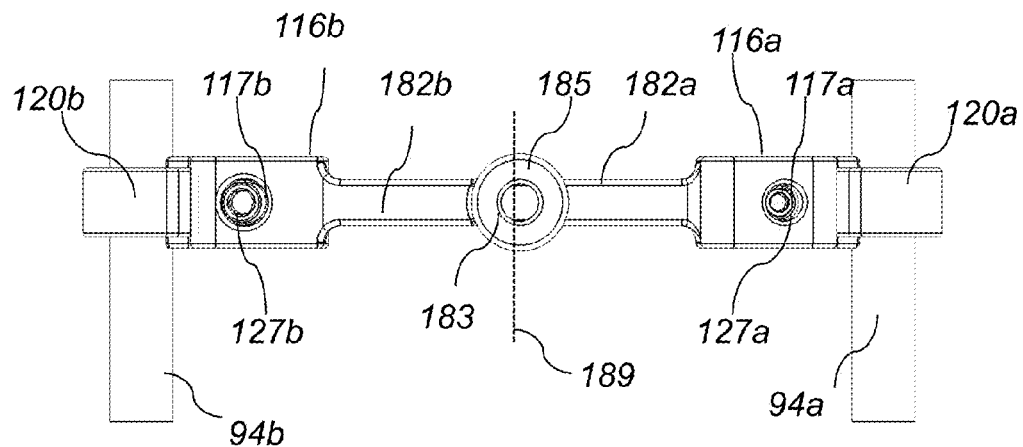
FIG. 9C is a top view of the translateral linking assembly of FIG. 9A.
Figure 9D:
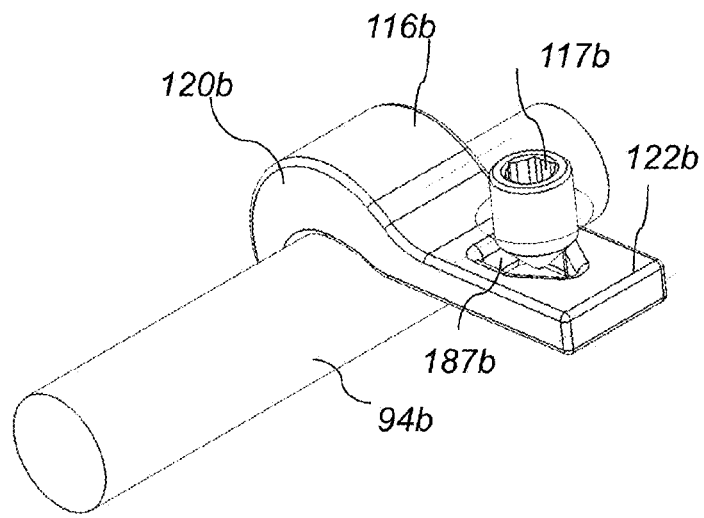
FIG. 9D is an enlarged view of the hook connector in the assembly of FIG. 9A in the rod engaged position.

Referring to FIG. 9A, FIG. 9B, FIG. 9C, and FIG. 9D, in another embodiment, translateral linking assembly 180 includes a main body that is made of two separate components 182a, 182b that are slidably connected to a cylindrical component 185. In this case, the ends 188a, 188b of components 182a and 182b are inserted into a side opening 181 formed in the cylindrical component 185 and are secured with a locking setscrew 183. End 188b slides on top of end 188a and both ends 188a, 188b slide into and out of opening 181. The length of the linking assembly 180 is adjusted by sliding components 182a, 182b into or out of the opening 181. Cylindrical component 185 also has a top through-opening 186, dimensioned to receive setscrew 183. Components 182a, 182b are flat, narrow, plate like and are slidably connected to hooked rod connectors 116a, 116b, respectively. Hooked rod connectors 116a, 116b include hook ends 120a, 120b, and flat ends 122a, 122b, respectively, as shown in FIG. 9D. The distal ends 184a, 184b of flat component 182a, 182b include side openings 198a, 198b, and through openings 127a, 127b, respectively. The flat ends 122a, 122b of the hooked rod connectors 116a, 116b include through-opening 187a, 187b, respectively. The flat ends 122a, 122b are inserted into side openings 198a, 198b, respectively, and are arranged within the side openings 198a, 198b so that through-openings 187a, 187b are concentric with the through-openings 127a, 127b of the distal ends 184a, 184b, respectively. Rods 94a, 94b are inserted in the space defined by the hooks ends 120a, 120b, and protrusions 199a, 199b of the distal ends 184a, 184b, respectively, as shown in FIG. 9B. The flat ends 122a, 122b of the hooked rod connectors 116a, 116b and rods 94a, 94b are secured in place by setscrews 117a, 117b that are screwed into the concentrically arranged through-openings 127a, 127b and 187a, 187b, respectively. In this embodiment, the geometry of openings 187a, 187b is tapered in the direction towards the midline 189, as shown in FIG. 9D, so that when the setscrews 117a, 117b are screwed into the openings 187a, 187b, they ramp the hook connectors 116a, 116b and the attached rods 94a, 94b, toward the midline 189.

Several embodiments of the present invention have been described. Nevertheless, it will be understood that various modifications may be made without departing from the spirit and scope of the invention. Accordingly, other embodiments are within the scope of the following claims.

What is claimed is:

1. A connector assembly for translateral linking of bilateral spinal fixation rods comprising:
a first component comprising an elongated body having first and second ends, wherein the first end of the first component is configured to connect to a first spinal fixation rod;
a second component comprising an elongated body having first and second ends, wherein the first end of the second component is configured to connect to a second spinal fixation rod; and
wherein the second end of the first component is configured to be slidably connected to the second end of the second component via a cylindrical component;
wherein the cylindrical component comprises a side through-opening and wherein the second ends of the first and second components are configured to be inserted into the side through-opening of the cylindrical component, and wherein a length of the connector assembly is adjusted by sliding the first and/or second components into or out of the side through-opening of the cylindrical component; and
wherein the second end of the first component is configured to slide within the side through-opening of the cylindrical component adjacent to the second end of the second component;
wherein the elongated body of the first component is flat, narrow and plate-shaped and the first end of the first component comprises a side opening and a through-opening and wherein the connector assembly further comprises a first hooked connector and wherein the first hooked connector comprises a hook end, a flat end and a through-opening, and wherein the flat end of the first hooked connector is configured to be inserted into the side opening of the first end of the first component and the through-opening of the hooked connector is arranged concentrically with the through-opening of the first end of the first component;

wherein the first spinal fixation rod is configured to be held and secured within the hook end of the first hooked connector and the hooked connector is secured to the first end of the first component via a set-screw configured to be threaded into the concentrically arranged through-openings of the first end of the first component and the hooked connector; and wherein the through-opening of the hooked connector is tapered and wherein tightening of the set-screw moves the hooked connector and the first spinal fixation rod towards a midline of the connector assembly.

2. The connector assembly of claim 1, further comprising a locking setscrew and wherein the second ends of the first and second components are secured to the cylindrical component via the locking setscrew.

3. The connector assembly of claim 2, wherein the cylindrical component further comprises a top through-opening dimensioned to receive the locking setscrew.

4. The connector assembly of claim 2, wherein the elongated body of the second component is flat, narrow and plate-shaped and the first end of the second component comprises a side opening and a through-opening and wherein the connector assembly further comprises a second hooked connector and wherein the second hooked connector comprises a hook end, a flat end and a through-opening, and wherein the flat end of the second hooked connector is configured to be inserted into the side opening of the first end of the second component and the through-opening of the second hooked connector is arranged concentrically with the through-opening of the first end of the second component.

5. The connector assembly of claim 4, wherein the second spinal fixation rod is configured to be held and secured within the hook end of the second hooked connector and the second hooked connector is secured to the first end of the second component via a set-screw configured to be threaded into the concentrically arranged through-openings of the first end of the second component and the second hooked connector; and wherein the through-opening of the second hooked connector is tapered and wherein tightening of the set-screw moves the second hooked connector and the second spinal fixation rod towards the midline of the connector assembly.

6. The connector assembly of claim 1, wherein the elongated body of the second component is flat, narrow and plate-shaped and the first end of the second component comprises a hook and a first through-opening, and wherein the second spinal fixation rod is configured to be held within the hook and to be secured to the first end of the second component via a set screw configured to be threaded into the first through-opening of the first end of the second component.

7. A connector assembly for translateral linking of bilateral spinal fixation rods comprising:

a first component comprising an elongated body having first and second ends, wherein the first end of the first component is configured to connect to a first spinal fixation rod;

a second component comprising an elongated body having first and second ends, wherein the first end of the second component is configured to connect to a second spinal fixation rod;

wherein the first end of the first component comprises a side opening and a through-opening and wherein the connector assembly further comprises a first hooked connector and wherein the first hooked connector comprises a hook end, a flat end and a through-opening, and wherein the flat end of the first hooked connector is configured to be inserted into the side opening of the first end of the first component and the through-opening of the first hooked connector is arranged concentrically with the through-opening of the first end of the first component;

wherein the first spinal fixation rod is configured to be held and secured within the hook end of the first hooked connector and the first hooked connector is secured to the first end of the first component via a set-screw configured to be threaded into the concentrically arranged through-openings of the first end of the first component and the first hooked connector; and wherein the through-opening of the first hooked connector is tapered and wherein tightening of the set-screw moves the first hooked connector and the first spinal fixation rod towards a midline of the connector assembly; and wherein the second end of the second component comprises a cylindrical component and wherein the cylindrical component comprises a side through-opening and wherein the second end of the first component is configured to be inserted into the side through-opening of the cylindrical component and is secured to the cylindrical component via a locking setscrew, and wherein a length of the connector assembly is adjusted by sliding the first component into or out of the side through-opening of the cylindrical component.

8. The connector assembly of claim 7, wherein the first end of the second component comprises a side opening and a through-opening and wherein the connector assembly further comprises a second hooked connector and wherein the second hooked connector comprises a hook end, a flat end and a through-opening, and wherein the flat end of the second hooked connector is configured to be inserted into the side opening of the first end of the second component and the through-opening of the second hooked connector is arranged concentrically with the through-opening of the first end of the second component;

wherein the second spinal fixation rod is configured to be held and secured within the hook end of the second hooked connector and the second hooked connector is secured to the first end of the second component via a set-screw configured to be threaded into the concentrically arranged through-openings of the first end of the second component and the second hooked connector; and wherein the through-opening of the second hooked connector is tapered and wherein tightening of the set-screw moves the second hooked connector and the second spinal fixation rod towards a midline of the connector assembly.

* * * * *